United States Patent [19]

Edwards et al.

[11] 4,348,322

[45] Sep. 7, 1982

[54] DIOXOLANE DERIVATIVES

[75] Inventors: Philip N. Edwards; David M. G. Martin, both of Stockport, England

[73] Assignee: Imperial Chemical Industries Limited, London, England

[21] Appl. No.: 242,529

[22] Filed: Mar. 11, 1981

[30] Foreign Application Priority Data

Apr. 3, 1980 [GB] United Kingdom ................. 8011378

[51] Int. Cl.³ .......................................... C07D 317/34
[52] U.S. Cl. .................................. 549/296; 562/469; 568/428
[58] Field of Search ....................................... 260/340.2

[56] References Cited

U.S. PATENT DOCUMENTS 3,299,127  1/1967  Zienty .
3,303,202  2/1967  Gallo et al. ...................... 260/340.2

FOREIGN PATENT DOCUMENTS 9306  2/1980  European Pat. Off. .
1140748  1/1969  United Kingdom .

OTHER PUBLICATIONS

J. American Chem. Soc., 1942, 64, 1567–1571, 1955, 77, 3131–3132, Fuson and Rachlin.

Primary Examiner—Ethel G. Love
Attorney, Agent, or Firm—Cushman, Darby & Cushman

[57] ABSTRACT

The invention is concerned with novel dioxolane derivatives of the formula:

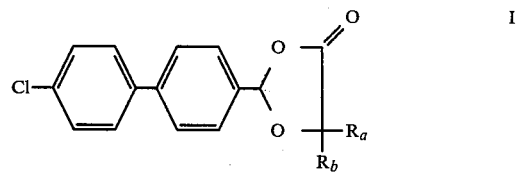

in which $R_a$ is hydrogen or (1–4C)alkyl and $R_b$ is (1–4C)alkyl or phenyl optionally bearing a halogeno substituent; their production; and their use for the manufacture of certain known anti-arthritic acids of the formula:

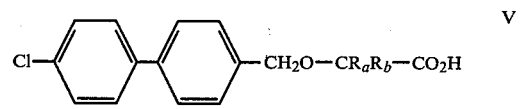

and, in particular, those acids in which $R_a=R_b=$methyl or $R_a=$ethyl and $R_b=$phenyl, by a novel reduction process. The preferred reduction procedures involve the use of an alkali metal borohydride or cyanoborohydride in the presence of a noble metal catalyst, or the use of an α-branched alkyl or cycloalkyl Grignard agent.

The use of the derivatives of formula I avoids the need for potentially toxic reagents and reactive intermediates in the previously known processes for the production of the acids of formula V.

4 Claims, No Drawings

DIOXOLANE DERIVATIVES

This invention relates to novel dioxolane derivatives which are useful as chemical intermediates, to processes for their manufacture and to processes for their conversion to valuable end-products. More particularly, the invention concerns 2-biphenylyl-1,3-dioxolan-4-one derivatives which are convertible to known benzyloxyacetic acid derivatives which are useful as anti-arthritic agents.

According to the invention there is provided a 2-biphenylyl-1,3-dioxalan-4-one of the formula:

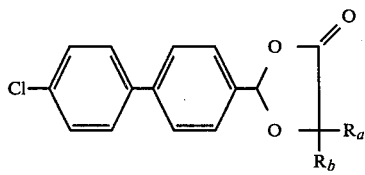   I wherein $R_a$ is hydrogen or a (1–4 C)alkyl radical, and $R_b$ is a (1–4 C)alkyl radical or a phenyl radical optionally bearing a halogeno radical.

A particular value for $R_a$ or $R_b$ when it is a (1–4 C)alkyl radical is, for example, a methyl or ethyl radical.

A particular value for an optional halogeno radical present on $R_b$ is for example, a fluoro, chloro or bromo radical.

A particular value for $R_b$ when it is a phenyl radical optionally bearing a halogeno radical is, for example, a phenyl, 4-fluorophenyl, 4-chlorophenyl or 4-bromophenyl radical.

Specific groups of compounds of formula I which are preferred are as follows:

(a) those compounds wherein both $R_a$ and $R_b$ are the same (1–4 C) radical; and (b) those compounds wherein $R_a$ is hydrogen or a methyl or ethyl radical and $R_b$ is a phenyl or 4-chlorophenyl radical.

Certain 1,3-dioxolan-4-ones having some structural similarity with the compounds of formula I have been described as chemical intermediates (U.S. Pat. No. 3,299,127).

Preferred intermediates of formula I are the compounds 2-[4-(4-chlorophenyl)phenyl]-5,5-dimethyl-1,3-dioxolan-4-one and 2-[4-(4-chlorophenyl)phenyl]-5-ethyl-5-phenyl-1,3-dioxolan-4-one.

It will be apparent that those compounds of formula I wherein $R_a$ and $R_b$ are the same possess one asymmetric carbon atom and that those compounds of formula I wherein $R_a$ and $R_b$ are different possess two asymmetric carbon atoms. The compounds of formula I may therefore exist in racemic and optically active forms in any of which they may be used in the processes of the invention referred to hereinafter.

It is known that, amongst others, compounds of the formula:

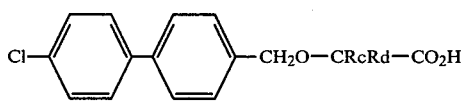   II wherein Rc is hydrogen or a (1–4 C)alkyl radical and Rd is a (1–4 C)alkyl radical, and the esters, amides and salts thereof possess anti-arthritic properties in addition to the property of lowering the level of at least one biochemical factor believed to be involved in atherosclerotic disease, and that a particular preferred compound of formula II is 2-[4-(4-chlorophenyl)benzyloxy]-2-methylpropionic acid (U.K. patent specification Ser. No. 1,140,748).

It is also known that compounds of the formula:

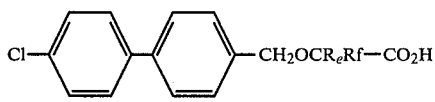   III wherein $R_e$ is hydrogen or a (1–4 C)alkyl radical and Rf is a phenyl radical optionally bearing a halogeno radical, and the esters and salts thereof, possess anti-arthritic properties, and that one particularly preferred compound of formula III is 2-[4-(4-chlorophenyl)benzyloxy]-2-phenylbutyric acid (European patent application, publication No. 9306A1).

Hitherto the compounds of formula II and III have only been described as obtainable by routes involving the use of the reactive intermediate 4-(4-chlorophenyl)-benzyl chloride, which is itself formed by a process using potentially toxic chloromethyl ethers. However, we have now discovered that the novel intermediates of the invention may be converted to the known useful carboxylic acids of formula II and III, or base-addition salts thereof, by a reduction process. This general process is provided as a feature of the invention and is illustrated by the following individual procedures wherein $R_a$, $R_b$, Rc, Rd, $R_e$ and Rf have the meanings defined hereinbefore:

(a) Reacting an intermediate of the formula I with an alkali metal borohydride or cyanoborohydride.

This procedure may be performed at a temperature in the range, for example, 20°–150° C., and preferably in the presence of a solvent or diluent, for example dimethyl formamide, water, a (1–4 C)alkanol such as ethanol, chlorobenzene or toluene, or a mixture of two or more such solvents. Specific preferred solvent combinations are, for example, a mixture of dimethylformamide and chlorobenzene, and a mixture of ethanol and water.

The borohydride reducing agent is conveniently for example, sodium or potassium borohydride or cyanoborohydride. A noble metal catalyst, for example palladium on charcoal is preferably also present, and the process is conveniently performed in the pH range, for example, pH 4.0–10.0 and preferably in the range pH 7.0–10.0. A particularly suitable reaction mixture pH may be conveniently obtained for example by passing carbon dioxide gas into the reaction mixtures before the addition of the reducing agent.

This procedure is particularly suitable for the production of compounds of formula II.

(b) Reacting an intermediate of the formula I with a Grignard reagent of the formula Rg.MgX wherein Rg is an α-branched chain alkyl or cycloalkyl radical of up to 10 carbon atoms and X is a halogeno radical.

A particular value of Rg is, for example, a t-butyl, 1-methylcyclohexyl or 1,1,3,3-tetramethylbutyl radical, of which a t-butyl radical is preferred.

A particular value for X is, for example, a chloro or bromo radical.

The procedure is preferably carried out at a reduced temperature, for example in the range −70° to 30° C. and, more particularly at a temperature in the range, for example, −50° to 20° C. A solvent or diluent, for example an organic ether such as diethyl ether, 1,2-dimethoxyethane, methoxybenzene 1,4-dioxan, methyl-t-butylether or tetrahydrofuran, or a mixture of one or more thereof, is also present optionally diluted with a hydrocarbon solvent or diluent for example hexane, octane, cyclohexane, toluene or chlorobenzene. The Grignard reagent is preferably present in excess.

This procedure is particularly suitable for the production of compounds of formula III as defined hereinbefore.

It is known that certain dioxolanones such as 2,2-dimethyl-5-phenyl-1,3-dioxolan-4-one are reductively cleaved by reaction with t-butyl magnesium chloride to give alkanoic acid derivatives (R. C. Fuson and A. I. Rachlin, *J. Amer. Chem. Soc.*, 1942, 64, 1567–1571). However it is also known that certain other dioxolanones such as 2,5-diphenyl-1,3-dioxolan-4-one are resistant to reductive cleavage (R. C. Fuson and D. E. Brasure, *J. Amer. Chem. Soc.* 1955, 77, 3131–3132). Accordingly the production of significant quantities of the compounds of formula II and III by procedure (b) is in itself unexpected.

(c) Reducing an intermediate of the formula I with gaseous hydrogen in the presence of a metal catalyst.

A suitable metal catalyst is, for example, a noble metal hydrogenation catalyst, for example palladium or platinum conveniently on a carbon support, or nickel.

This procedure is preferably carried out in the presence of a suitable solvent or diluent, for example a (1–4 C)alkanol such as ethanol, a (1–4 C)alkanoic acid such as acetic acid, or water, or a mixture of such solvents, and at a temperature in the range, for example, 15° to 30° C. In general, however, the reduction should be carried out using the mildest conditions possible to minimise any concomitant loss of the chloro radical.

(d) Reducing an intermediate of the formula I with an alkali metal dithionite.

A suitable alkali metal dithionite is, for example, sodium dithionite, and the procedure is normally carried out in the presence of a suitable aqueous solvent or diluent, for example in a (1–4 C)alkanol, such as ethanol, mixed with water and at a temperature in the range, for example, 10° to 40° C.

(e) Reducing an intermediate of the formula I with titanium trichloride.

This procedure is preferably carried out in a suitable aqueous solvent or diluent, for example in a (1–4 C)alkanol such as ethanol, mixed with water. The procedure is preferably performed at a temperature in the range, for example, 10° to 40° C., and conveniently at a pH in the range, for example pH 2–7 and preferably at or near pH 5, for example in the presence of a suitable buffer such as ammonium acetate.

Of the above procedures, (b) is particularly preferred.

It will be appreciated that any optical asymmetry present at the 2-position of the 1,3-dioxolan-4-ones of formula I is lost during reduction to the compounds of formula II or III, but that, by contrast, any optical asymmetry present at the 5-position (i.e. in compounds of formula I wherein $R_a$ and $R_b$ are different) can be retained so that an optically active compound of formula III may be obtained by a process of the invention if required.

It will also be appreciated that the acids of formula II or III are, in general, initially obtained as their base-addition salts. However they may readily be isolated in free acid form by acidification in conventional manner.

The intermediates of formula I may be obtained by procedures well known in the art of heterocyclic chemistry for the preparation of chemically analogous compounds. Such processes are provided as a further feature of the invention. One such preferred process for the production of intermediates of formula I defined hereinbefore comprises condensing 4-(4-chlorophenyl)benzaldehyde, or a hydrate, hemiacetal or acetal thereof, with a hydroxyalkanoic acid of the formula:

$$HO-Cr_aR_b-CO_2H \qquad IV$$

or a (1–6 C)alkyl ester thereof, wherein $R_a$ and $R_b$ have the meanings defined hereinbefore.

A suitable (1–6 C)alkyl ester is, for example, a methyl or ethyl ester and a suitable hemiacetal or acetal is, for example, one derived from a (1–4 C)alkanol, for example from methanol or ethanol. However, in general it is preferred to react the free hydroxyalkanoic acid of formula IV with 4-(4-chlorophenyl)benzaldehyde itself.

The reaction is preferably performed in the presence of an acid, for example p-toluenesulphonic acid, sulphuric acid, or the free acid form of a cationic ion exchange resin such as a sulphonated polystyrene, and at a temperature in the range, for example, 40° to 150° C. Alternatively, the acid may be a Lewis acid for example boron-trifluoride etherate, in which case the reaction may be performed at a temperature in the range for example, 0° to 30° C.

The reaction may be conveniently carried out in a solvent or diluent, for example toluene, chlorobenzene or cyclohexane, and the water which is formed during the reaction may be removed, for example by azeotropic distillation.

The 4-(4-chlorophenyl)benzaldehyde, which is believed to be a novel compound, may be obtained by conventional procedures known for the production of analogous compounds. Thus, it may be obtained by oxidation of the known compounds 4-(4-chlorophenyl)-benzyl chloride (using dimethylsulphoxide) or 4-(4-chlorophenyl)benzyl alcohol (using nitric acid or ceric ammonium nitrate) in both cases using a similar procedure to that known for the preparation of analogous benzaldehydes. Alternatively, and preferably, it may be obtained by a Gatterman-Koch formylation of 4-chlorobiphenyl, for example as described in Example I hereinafter. This latter procedure is especially advantageous for large scale use since it avoids the use of potentially toxic chloromethyl ethers which have so far been described in the known synthesis of 4-(4-chlorophenyl)-benzyl chloride by chloromethylation of 4-chlorobiphenyl (U.K. patent specification Serial No. 1,140,748).

Accordingly there is further provided as a feature of the invention a process for the production of a compound of the formula:

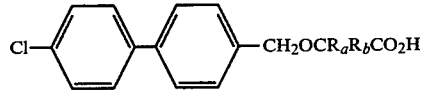

$$Cl-\phantom{x}-\phantom{x}-CH_2OCR_aR_bCO_2H \qquad V$$

wherein $R_a$ and $R_b$ have the meanings defined hereinbefore, or a base-addition salt thereof, characterised by carrying out the following steps in sequence:

(i) reacting 4-(4-chlorophenyl)benzaldehyde or a hydrate, hemiacetal or acetal thereof, with a hydroxy acetic acid derivative of the formula:

$$HO-CR_aR_b-CO_2H \qquad IV$$

or a (1-6 C)alkyl ester thereof, to give an intermediate of the formula:

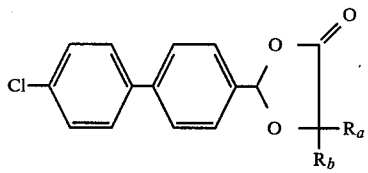

and (ii), reducing the intermediate of formula I formed in (i), for example, using one of the procedures (a)-(e) described hereinbefore;

whereafter when a base-addition salt is required the free acid of formula V is reacted with a suitable base using a conventional procedure.

The conditions necessary for carrying out step (i) are those previously described hereinbefore.

A particularly preferred process of the invention for the production of a compound of the formula II defined hereinbefore, and of 2-[4-(4-chlorophenyl)benzyl]-2-methylpropionic acid in particular uses steps (i) and (ii) referred to above in which the reduction procedure involves the use of either an alkali metal borohydride or cyanoborohydride in the presence of a noble metal catalyst, or a Grignard reagent of the formula Rg.MgX in which Rg is an α-branched chain alkyl or cycloalkyl radical, for example, a t-butyl or 1-methylcyclohexyl radical, and X is a halogeno radical.

A particularly preferred process of the invention for the production of a compound of the formula III defined hereinbefore, and of 2-[4-(4-chlorophenyl)benzyl]-2-phenylbutyric acid in particular uses steps (i) and (ii) referred to above in which the reduction procedure involves the use of a Grignard reagent of the formula Rg.MgX wherein Rg is an α-branched chain alkyl or cycloalkyl radical of up to 10 carbon atoms, for example a t-butyl or 1-methylcyclohexyl radical, and X is a halogeno radical.

These processes are advantageous over those known in the art since they avoid the use of potentially toxic reagents and reactive intermediates.

The invention is illustrated but not limited by the following Examples, in which unless otherwise stated:
(i) all evaporations were by rotary evaporation in vacuo:
(ii) reactions were carried out at room temperature (15°-25° C.);
(iii) petroleum ether, b.p. 100°-120° C. is referred to as "100-120 petrol"; and
(iv) yields, where given, are provided for illustrative purposes only and are not to be understood as the maximum attainable.

EXAMPLE 1

A mixture of 4-(4-chlorophenyl)benzaldehyde (15.0 g.), 2-hydroxy-2-methylpropionic acid (10.0 g.) and p-toluenesulphonic acid monohydrate (0.2 g.) was heated in toluene (200 ml.) under reflux for 6 hours with continuous removal of water by azeotropic distillation. The solution was then cooled, washed with 10% w/v sodium hydrogen carbonate solution (100 ml.) and then with water (2×100 ml.) before it was dried (Na₂SO₄). The dried toluene solution was filtered and evaporated to give 2-[4-(4-chlorophenyl)phenyl]-5,5-dimethyl-1,3-dioxolan-4-one (14.6 g.), m.p. 108°-110° C. (after recrystallisation from cyclohexane and then from toluene).

The 4-(4-chlorophenyl)benzaldehyde was obtained as follows:

A mixture of 4-chlorobiphenyl (18.8 g.) and aluminium chloride (29.5 g.) was stirred in chlorobenzene (150 ml.) at 55°-60° C., in a pressure vessel. The vessel was pressurised to 2 bars with an equimolar mixture of carbon monoxide and hydrogen chloride (prepared by the action of 98-100% formic acid on chlorosulphonic acid). These reaction conditions were maintained for a period of 4 days. After this time the reaction mixture was added, with stirring, to a mixture of ice (500 g.) and water (500 ml.). The organic phase was separated and the aqueous phase was extracted with chlorobenzene (50 ml.). The combined organic phases were then washed successively with 2 M hydrochloric acid (100 ml.) and water (2×100 ml.), and evaporated onto chromotographic silica gel (40 g.). The residue obtained was added to the top of a column of chromatographic silica gel (160 g.) made up in carbon tetrachloride. The column was then washed through with carbon tetrachloride (2000 ml.) and then eluted with chloroform (2000 ml.) The fractions containing material of $R_f$ value (system: SiO₂; methylene chloride/carbon tetrachloride 1:1 v/v) were combined and evaporated to give 4-(4-chlorophenyl)benzaldehyde (7.3 g.) m.p. 108°-112° C. (after recrystallisation from aqueous acetonitrile).

EXAMPLES 2-3

Using a similar procedure to that described in Example 1, the following compounds of formula I were obtained:

2-[4-(4-chlorophenyl)phenyl]-5-ethyl-5-phenyl-1,3-dioxolan-4-one (Example 2) in 25% yield as a solid, m.p. 80°-83° C. (after recrystallisation from methanol) starting from 2-hydroxy-2-phenylbutyric acid;

2-[4-(4-chlorophenyl)phenyl]-5-phenyl-1,3-dioxolan-4-one (Example 3) in 30% yield as a solid, m.p. 121°-130° C. (after recrystallisation from toluene/cyclohexane) containing two diastereoisomers in the approximate ratio 2:1 (as indicated by NMR spectroscopy) and starting from (S)-mandelic acid.

EXAMPLE 4

A solution of 2-[4-(4-chlorophenyl)phenyl]-5,5-dimethyl-1,3-dioxolan-4-one (1.0 g.) in chlorobenzene (10 ml.) was added in portions during 30 minutes to a solution of sodium borohydride (0.12 g.) in N,N-dimethylformamide (15 ml.) maintained at 90° C. After a further 30 minutes the reaction mixture was added to water (30 ml.) and the pH of the mixture adjusted to 4 with acetic acid. This mixture was extracted with toluene (2×20 ml.). The combined extracts were washed with water, dried (Na₂SO₄) and evaporated. The residue was purified by preparative thin layer chromatography on silica coated plates (4, 20 cm×20 cm×2.5 mm thick), using a 1:10 v/v mixture of methanol/chloroform as eluant. There was thus obtained 2-[4-(4-chlorophenyl)benzyloxy]-2-methylpropionic acid, m.p. 154°-155° C., in 10% yield.

EXAMPLE 5

A stirred solution of 2-[4-(4-chlorophenyl)phenyl]-5,5-dimethyl-1,3-dioxolan-4-one (5.0 g.) in toluene (35 ml.) was cooled to 0° to 5° C. and maintained at that temperature during the dropwise addition of a solution of t-butylmagnesium chloride [obtained by a conventional procedure (Org. Synthesis, Col. Vol. I, 524) from t-butyl chloride (7.5 ml.) and magnesium turnings (1.22 g.) heated at reflux for 5 hours in dry diethyl ether (35 ml.), using 1,2-dibromoethane (0.05 ml.) as initial activator]. The addition was completed within 30 minutes and after a further 15 minutes stirring at 0° to 5° C. the reaction mixture was added with stirring to an excess of 1.5 M hydrochloric acid (100 ml.). The organic phase was separated, washed free of acid with water and then dried (MgSO$_4$), filtered and evaporated. The pale yellow solid residue was recrystallised from toluene to give 2-[4-(4-chlorophenyl)benzyloxy]-2-methylpropionic acid, m.p. 154°–155° C. in 52% yield.

EXAMPLE 6

A mixture of 4-(4-chlorophenyl)benzaldehyde (8.7 g.), 2-hydroxy-2-phenylbutyric acid (8.6 g.) and p-toluenesulphonic acid monohydrate (0.76 g.) was heated in cyclohexane (160 ml.) under reflux for 3 hours with continuous removal of water by azeotropic distillation. The mixture was then cooled, diluted with ethyl acetate (20 ml.) and washed with 10% w/v potassium carbonate solution (3×50 ml.) and then with water (2×50 ml.). The solution was dried (Na$_2$SO$_4$), filtered, evaporated and triturated with methanol to give 2-[4-(4-chlorophenyl)phenyl]-5-ethyl-5-phenyl-1,3-dioxolan-4-one (14.7 g.), m.p. 80°–83° C. (after recrystallisation from methanol).

EXAMPLE 7

To a stirred solution of 4-(4-chlorophenyl)benzaldehyde (2.16 g.) and 2-hydroxy-2-phenylbutyric acid (1.8 g.) in anhydrous diethyl ether (50 ml.) was added boron trifluoride etherate (2.2 g.). After stirring at room temperature for 12 hours, the solution was washed with 10% w/v sodium acetate solution (2×20 ml.) and then with water (2×20 ml.) and dried (Na$_2$SO$_4$). The solution was filtered and evaporated to give an oil which on crystallisation from methanol gave 2-[4-(4-chlorophenyl)phenyl]-5-ethyl-5-phenyl-1,3-dioxolan-4-one (1.7 g.) m.p. 80°–83° C.

EXAMPLE 8

To a cold (−50° C.) solution of t-butyl magnesium chloride, prepared from magnesium turnings (1.22 g.) and a solution of t-butyl chloride (6.40 g.) in anhydrous ether (40 ml.), was added a solution of 2-[4-(4-chlorophenyl)phenyl]-5-ethyl-5-phenyl-1,3-dioxolan-4-one (4.7 g.) in anhydrous ether (100 ml.). The mixture was stirred at room temperature for 16 hours and then poured into dilute hydrochloric acid (200 ml., 1.5 M). The organic phase was separated and the aqueous phase was extracted with ether (2×50 ml.). The combined organic phases were washed with water (2×50 ml.) dried (Na$_2$SO$_4$) and evaporated to give a yellow oil (5.85 g.). The oil crystallised on treatment with cyclohexane to give 2-[4-(4-chlorophenyl)benzyloxy]-2-phenylbutyric acid (1.2 g.), m.p. 128°–130° C. (after recrystallisation from ethyl acetate/cyclohexane).

EXAMPLE 9

A stirred suspension of 2-[4-(4-chlorophenyl)phenyl]-5-ethyl-5-phenyl-1,3-dioxolan-4-one (3.8 g.) in 100-120 petrol (40 ml.) was cooled to 5° to 10° C. and maintained at that temperature during the dropwise addition of a solution of 1-methylcyclohexylmagnesium chloride [obtained by a conventional procedure from 1-methylcyclohexyl chloride (7.8 g.) and magnesium turnings (1.36 g.) in dry tetrahydrofuran (20 ml.) at 30°–35° C. using 1,2-dibromoethane (0.05 ml.) as initiator]. The addition was completed within 30 minutes and after a further 90 minutes stirring at room temperature, a solution of dilute hydrochloric acid [prepared from concentrated hydrochloric acid (5 ml.) and water (10 ml.)] was added, maintaining the temperature of the reaction mixture below 30° C. The organic phase was separated, washed with water, and distilled (still-head temperature 105° C.) until 32 ml. of distillate had collected. The residual liquid was allowed to cool to room temperature and then stirred for 14 hours. The resultant solid was collected, washed with 100–120 petrol (10 ml.) dried at 70° C. and recrystallised from ethylbenzene to give 2-[4-(4-chlorophenyl)benzyloxy]-2-phenylbutyric acid (1.0 g.), m.p. 128°–130° C.

EXAMPLE 10

A mixture of 4-(4-chlorophenyl)benzaldehyde (20.3 g.), 2-hydroxy-2-phenylbutyric acid (20.4 g.) and p-toluenesulphonic acid monohydrate (1.5 g.) was heated in chlorobenzene (180 ml.) at reduced pressure (160 mm. Hg) under reflux for four hours and with continuous removal of water by azeotropic distillation. The mixture was then cooled, added to water (120 ml.) and the pH of the aqueous phase adjusted to 7 to 8 with caustic soda liquor.

The chlorobenzene was removed by azeotropic distillation with water and the resulting aqueous mixture was extracted with 100–120 petrol (260 ml.) at 80° C. After washing with water, the organic phase was dried by azeotropic distillation to give a suspension of 2-[4-(4-chlorophenyl)phenyl]-5-ethyl-5-phenyl-1,3-dioxolan-4-one. To this suspension was added a solution of t-butyl magnesium chloride (35.2 g., estimated by compleximetric titration) in tetrahydrofuran (180 ml.) during 60 minutes. During this period the temperature was kept at 18° to 20° C. After stirring the suspension for a further 2 hours, dilute hydrochloric acid [prepared from concentrated hydrochloric acid (25 ml.) and water (50 ml.)] was added maintaining the temperature below 30° C. The organic phase was separated, washed with water (2×50 ml.) and then treated as described in Example 9. There was thus obtained 2-[4-(4-chlorophenyl)benzyloxy]-2-phenylbutyric acid (14.2 g.), m.p. 128°–130° C. (after recrystallisation from ethylbenzene).

EXAMPLE 11

Hydrogen gas was allowed to react with a stirred suspension of 2-[4-(4-chlorophenyl)phenyl]-5-ethyl-5-phenyl-1,3-dioxolan-4-one (3.8 g.) and 5% w/w palladium on carbon (0.2 g.) in ethanol (160 ml.) at 55° to 60° C. and atmospheric pressure for four hours. The mixture was diluted with toluene (50 ml.). The solid material was separated by filtration and the filtrate was evaporated. The resultant solid may be purified by high pressure liquid chromatography on "Spherisorb"* 5μ ODS solid phase using an eluant containing acetonitrile (62% v/v), water (37.9% v/v) and phosphoric acid (0.1% v/v) using ultraviolet absorbance at 262 μm for detection to give 2-[4-(4-chlorophenyl)benzyloxy]-2-phenylbutyric acid identical to that obtained in previous examples.

*["Spherisorb" is a trade-mark of Phase Separations Ltd., Deeside Industrial Estate, Queensferry, Clwyd, U.K.]

EXAMPLE 12

A stirred suspension of 2-[4-(4-chlorophenyl)phenyl]-5,5-dimethyl-1,3-dioxolan-4-one (100.0 g.), 5% w/w palladium on carbon (10 g.) in a mixture of ethanol (500 ml.) and water (1000 ml.) was cooled to 10° to 15° C. and treated with carbon dioxide gas. The temperature and gas flow were maintained during the addition of a solution of sodium borohydride (63.0 g.) in water (250 ml.) during 1 hour. After 5 hours at 15° to 20° C. the pH of the reaction mixture was adjusted to pH 12 with 47% w/w sodium hydroxide solution and diluted with ethanol (1000 ml.). The residue was separated by filtration and washed successively with ethanol (2×250 ml.) and water (2×250 ml.). The combined filtrate and washings were evaporated to about half volume and the pH adjusted to 3 with 34% w/w hydrochloric acid. The solid which formed was recrystallised twice from toluene to give 2-[4-(4-chlorophenyl)benzyloxy]-2-methylpropionic acid, (m.p. 154°-155° C.) in 42% yield.

EXAMPLE 13

Palladium on carbon (5% w/w, 0.1 g.) was added to a solution of 2-[4-(4-chlorophenyl)-phenyl]-5,5-dimethyl-1,3-dioxolan-4-one (0.3 g.) in ethanol (50 ml.). The suspension was treated with hydrogen gas at 25° C. and atmospheric pressure for 1.5 hours. The catalyst was removed by filtration and the filtrate evaporated. The residue was dissolved in toluene (10 ml.) and the solution obtained was extracted with 1 M sodium hydroxide solution (10 ml.). The aqueous extracts were acidified with 2 M hydrochloric acid and extracted with toluene (2×10 ml.). By evaporation of the toluene extracts, there may thus be obtained 2-[4-(4-chlorophenyl)benzyloxy]-2-methylpropionic acid, as a waxy solid equivalent to that obtained in Example 12.

EXAMPLE 14

A mixture of 4-(4-chlorophenyl)benzaldehyde (21.6 g.), 2-hydroxy-2-methylpropionic acid (10.2 g.) and cationic sulphonated polystyrene ion exchange resin ('AMBERLITE' *IR 120, free acid form; 2.0 g.) in chlorobenzene (125 ml.) was heated under reflux for 24 hours with continuous removal of water by azeotropic distillation. The mixture was cooled and the resin was separated by filtration. Pyridine (3 ml.) was added to the filtrate which was then evaporated. The residue was dissolved in hot 2-propanol (200 ml.). A small quantity of insoluble material was removed by filtration and the subsequent filtrate was allowed to cool to give 2-[4-(4-chlorophenyl)phenyl]-5,5-dimethyl-1,3-dioxolan-4-one (11.8 g.), m.p. 108°-110° C.

[*'Amberlite' is a trade-mark, the property of The Rohm-Haas Company, Philadelphia, USA].

EXAMPLE 15

A stirred solution of 1-methylcyclohexyl magnesium chloride in tetrahydrofuran [obtained by a conventional procedure similar to that used to make t-butyl magnesium chloride (see Example 5) but starting from 1-chloro-1-methylcyclohexane (33.9 g.) and magnesium turnings (4.82 g.) heated at 40° C. for 5 hours in tetrahydrofuran (117 ml.) using 1,2-dibromoethane (0.05 ml) as initiator] was cooled to 0° to 5° C. and maintained at that temperature during the dropwise addition of a solution of 2-[4-(4-chlorophenyl)phenyl]-5,5-dimethyl-1,3-dioxolan-4-one (15.0 g.) in chlorobenzene (100 ml.) under an argon atmosphere during 1 hour. After a further 45 minutes stirring at 0° to 5° C., the reaction mixture was added with stirring to an excess of 1.5 M hydrochloric acid (330 ml.) keeping the temperature below 20° C. The organic phase was separated, washed acid free with water and then heated at reflux for 10 minutes with 0.7 M aqueous potassium hydroxide (150 ml.). The aqueous layer was separated and acidified at 60° C. with concentrated hydrochloric acid (8.5 ml.) to give a solid precipitate which was collected by filtration, dried and re-crystallised from toluene (90 ml.). This gave 2-[4-(4-chlorophenyl)benzyloxy]-2-methylpropionic acid, m.p. 154°-155° C. in 50% yield.

EXAMPLE 16

A solution of 4-(4-chlorophenyl)benzaldehyde (41.5 g.) in chlorobenzene (250 ml.) containing in addition 2-hydroxy-2-methylpropionic acid (29.7 g.) and p-toluenesulphonic acid monohydrate (2.7 g.) was heated under reflux for 6 hours at reduced pressure (105° C., 313 mm Hg) with continuous removal of water by azeotropic distillation. The solution was then cooled, washed successively with 10% w/v sodium carbonate solution (500 ml.) and water (2×500 ml.), dried (MgSO$_4$), filtered and diluted with fresh chlorobenzene to a volume of 350 ml. to give a solution containing 14.3% w/v of 2-[4-(4-chlorophenyl)-phenyl]-5,5-dimethyl-1,3-dioxolanone-4-one, as estimated by gas-liquid chromatography. This solution (35 ml.) was added during 1 hour at 0° to 5° C. under an argon atmosphere to a stirred solution of t-butyl magnesium chloride [prepared from magnesium turnings (1.61 g.) and a solution of t-butyl chloride (9.33 ml.) in anhydrous ether (40 ml.)]. The mixture was stirred for 1 hour at 0° to 5° C. and then for a further 16 hours at room temperature before being poured into 1.5 M hydrochloric acid (100 ml.). The organic phase was separated and washed with water (2×100 ml.), dried (Na$_2$SO$_4$) and evaporated to give 2-[4-(4-chlorophenyl)benzyloxy]-2-methyl-propionic acid (9.23 g.), m.p. 154°-155° C., after recrystallisation from toluene.

What is claimed is:

1. A 2-biphenylyl-1,3-dioxolan-4-one of the formula:

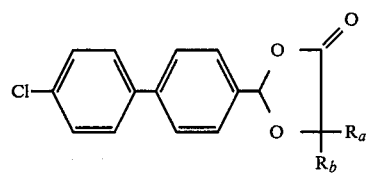

wherein $R_a$ is hydrogen or a (1-4 C)alkyl radical, and $R_b$ is a (1-4 C)alkyl radical or a phenyl radical optionally bearing a halogeno radical.

2. A compound as claimed in claim 1 wherein $R_a$ is hydrogen, or a methyl or ethyl radical, and $R_b$ is a methyl, ethyl, phenyl, or 4-halogenophenyl radical.

3. A compound selected from 2-[4-(4-chlorophenyl)-phenyl]-5,5-dimethyl-1,3-dioxolan-4-one, 2-[4-(4-chlorophenyl)phenyl]-5-methyl-5-phenyl-1,3-dioxolan-4-one, 2-[4-(4-chlorophenyl)phenyl]-5-ethyl-5-phenyl-1,3-dioxolan-4-one and 2-[4-(4-chlorophenyl)phenyl]-5-phenyl-1,3-dioxolan-4-one.

4. A compound according to claim 1, said compound being 2-[4-(4-chlorophenyl)phenyl]-5-ethyl-5-phenyl-1,3-dioxolan-4-one.

* * * * *